US011185093B2

(12) United States Patent
Köpsel

(10) Patent No.: US 11,185,093 B2
(45) Date of Patent: *Nov. 30, 2021

(54) PULVERULENT CAROTENOID PREPARATION FOR COLOURING DRINKS

(76) Inventor: Christian Köpsel, Weinheim (DE)

( * ) Notice: Subject to any disclaimer, the term of this patent is extended or adjusted under 35 U.S.C. 154(b) by 1363 days.

This patent is subject to a terminal disclaimer.

(21) Appl. No.: 12/744,571

(22) PCT Filed: Nov. 11, 2008

(86) PCT No.: PCT/EP2008/065285
§ 371 (c)(1),
(2), (4) Date: May 25, 2010

(87) PCT Pub. No.: WO2009/068432
PCT Pub. Date: Jun. 4, 2009

(65) Prior Publication Data
US 2010/0267838 A1   Oct. 21, 2010

Related U.S. Application Data

(63) Continuation of application No. PCT/EP2008/065285, filed on Nov. 11, 2008.

(30) Foreign Application Priority Data

Nov. 29, 2007 (EP) .................................... 07121904

(51) Int. Cl.
| A23K 20/179 | (2016.01) |
| A23K 40/10 | (2016.01) |
| A23K 20/174 | (2016.01) |
| A23L 29/219 | (2016.01) |
| A23L 33/105 | (2016.01) |
| A23L 33/155 | (2016.01) |
| A23L 33/10 | (2016.01) |
| A23P 10/47 | (2016.01) |

(52) U.S. Cl.
CPC .......... *A23K 20/179* (2016.05); *A23K 20/174* (2016.05); *A23K 40/10* (2016.05); *A23L 29/219* (2016.08); *A23L 33/10* (2016.08); *A23L 33/105* (2016.08); *A23L 33/155* (2016.08); *A23P 10/47* (2016.08); *A23V 2002/00* (2013.01); *A23V 2200/25* (2013.01)

(58) Field of Classification Search
CPC .................................................. A23K 20/179
See application file for complete search history.

(56) References Cited

U.S. PATENT DOCUMENTS

| 2,661,349 | A | 12/1953 | Caldwell |
| 3,110,598 | A | 11/1963 | Mueller et al. |
| 4,522,743 | A | 6/1985 | Horn et al. |
| 4,844,934 | A | 7/1989 | Lueddecke et al. |
| 5,028,625 | A | 7/1991 | Motola et al. |
| 5,078,980 | A | 1/1992 | Mullner et al. |
| 5,350,773 | A | 9/1994 | Schweikert et al. |
| 5,364,563 | A | 11/1994 | Cathrein et al. |
| 5,637,618 | A | 6/1997 | Kurtz et al. |
| 5,827,539 | A | 10/1998 | Gellenbeck |
| 5,863,953 | A | 1/1999 | Lüddecke et al. |
| 5,891,907 | A | 4/1999 | Kolter et al. |
| 5,968,251 | A | 10/1999 | Auweter et al. |
| 6,201,155 | B1 | 3/2001 | Burdet et al. |
| 6,224,876 | B1 | 5/2001 | Kesharial et al. |
| 6,235,315 | B1 | 5/2001 | Runge et al. |
| 6,287,615 | B1 | 9/2001 | Runge et al. |
| 6,639,113 | B2 | 10/2003 | Runge et al. |
| 7,070,812 | B2 | 7/2006 | Runge et al. |
| 2002/0110599 | A1* | 8/2002 | Auweter ................ A23K 1/001 424/499 |
| 2002/0128325 | A1 | 9/2002 | Runge et al. |
| 2002/0188019 | A1 | 12/2002 | Ley et al. |
| 2004/0033246 | A1 | 2/2004 | Naru et al. |
| 2005/0079223 | A1 | 4/2005 | Estrella De Castro et al. |
| 2005/0084462 | A1 | 4/2005 | Klingenberg |
| 2006/0035871 | A1 | 2/2006 | Auweter et al. |
| 2007/0054023 | A1 | 3/2007 | Bingley |
| 2008/0026124 | A1 | 1/2008 | Musaeus et al. |
| 2008/0113076 | A1 | 5/2008 | Klingenberg |
| 2008/0131515 | A1 | 6/2008 | Ogawa et al. |
| 2008/0193539 | A1 | 8/2008 | Voelker |
| 2008/0207775 | A1 | 8/2008 | Musaeus et al. |

(Continued)

FOREIGN PATENT DOCUMENTS

| CH | 418106 | 7/1966 |
| DE | 1211911 B | 3/1966 |

(Continued)

OTHER PUBLICATIONS

Manz, "Die anwendung und bedeutung von synthetischen carotinoiden in der lebens- und futtermittel-sowie in der pharmazeutischen industrie," Chimia, 1967, vol. 21, pp. 329-335.

U.S. Appl. No. 13/198,909, filed Aug. 5, 2011, Kopsel et al.

Bai, Y., Doctoral Thesis "Preparation and Structure of Octenyl Succinic Anhydride Modified Waxy Maize Starch, Microporous Starch and Maltodextrin," Department of Grain Science and Industry, College of Agriculture, Kansas State University, Manhattan, Kansas, 2008.

Drusch, S., et al., "Impact of Physicochemical Characteristics on the Oxidative Stability of Fish Oil Microencapsulated by Spray-Drying," J. Agric. Food Chem. 2007, vol. 55, pp. 11044-11051.

Ley, Jakob P., et al., New Bitter-Masking Compounds: Hydroxylated Benzoic Acid Amides of Aromatic Amines as Structural Analogues of Homeriodictyol, 2006, Journal of Agricultural and Food Chemistry, vol. 54, No. 22, pp. 8574-8579.

(Continued)

*Primary Examiner* — Rei Tsang Shiao
(74) *Attorney, Agent, or Firm* — Faegre Drinker Biddle & Reath LLP

(57) ABSTRACT

The present invention relates to pulverulent compositions of at least one carotenoid selected from the group consisting of β-carotene, astaxanthin, canthaxanthin, citranaxanthin, lycopene and lutein, a process for the production of these pulverulent compositions, and the use of the pulverulent compositions.

20 Claims, No Drawings

(56) References Cited

U.S. PATENT DOCUMENTS

| | | |
|---|---|---|
| 2010/0028444 A1 | 2/2010 | Matuschek et al. |
| 2010/0041607 A1 | 2/2010 | Jensen et al. |
| 2010/0047426 A1 | 2/2010 | Matuschek et al. |
| 2010/0120922 A1 | 5/2010 | Kopsel et al. |
| 2010/0267838 A1 | 10/2010 | Kopsel et al. |
| 2011/0207831 A1 | 8/2011 | Kopsel |

FOREIGN PATENT DOCUMENTS

| | | |
|---|---|---|
| DE | 3119383 A1 | 12/1982 |
| DE | 10059213 A1 | 6/2002 |
| DE | 10122898 A1 | 11/2002 |
| DE | 102004046026 A1 | 3/2006 |
| DE | 102005030952 A1 | 1/2007 |
| EP | 065193 A2 | 11/1982 |
| EP | 0065193 A2 | 11/1982 |
| EP | 0 239 086 A2 | 9/1987 |
| EP | 0410236 A2 | 1/1991 |
| EP | 0416236 A2 | 3/1991 |
| EP | 0 551 638 A1 | 7/1993 |
| EP | 0732064 A1 | 9/1996 |
| EP | 0800825 A1 | 10/1997 |
| EP | 0832569 A2 | 4/1998 |
| EP | 0848913 A2 | 6/1998 |
| EP | 937412 A1 | 8/1999 |
| EP | 0978508 A2 | 2/2000 |
| EP | 1213013 A2 | 6/2002 |
| EP | 1219292 A1 | 7/2002 |
| EP | 1228705 A2 | 8/2002 |
| EP | 1 258 200 A2 | 11/2002 |
| EP | 1 460 060 A1 | 9/2004 |
| EP | 1 875 814 A1 | 1/2008 |
| EP | 1 927 287 A1 | 6/2008 |
| EP | 1952845 A1 | 8/2008 |
| GB | 885677 | 12/1961 |
| GB | 970363 A | 9/1964 |
| JP | 63137657 A | 6/1988 |
| JP | 2025428 A | 1/1990 |
| JP | 4-262758 A | 9/1992 |
| JP | 7-99924 A | 4/1995 |
| JP | 7-083684 B2 | 9/1995 |
| JP | 2001226293 A | 8/2001 |
| JP | 2004-196673 A | 7/2004 |
| WO | WO-91/06292 A1 | 5/1991 |
| WO | WO-93/04598 A1 | 3/1993 |
| WO | WO-94/19411 A1 | 9/1994 |
| WO | WO-96/13178 A1 | 5/1996 |
| WO | WO-96/23420 A1 | 8/1996 |
| WO | WO-03/066583 A1 | 8/2003 |
| WO | WO-03/086293 A2 | 10/2003 |
| WO | WO-03/102116 A2 | 12/2003 |
| WO | WO-2005/060923 A1 | 7/2005 |
| WO | WO-2006/032399 A2 | 3/2006 |
| WO | WO-2006/125591 A1 | 11/2006 |
| WO | WO-2007/003543 A1 | 1/2007 |
| WO | WO-2007/009601 A1 | 1/2007 |
| WO | WO-2007/020057 A1 | 2/2007 |
| WO | WO-2007/045488 A1 | 4/2007 |
| WO | WO-2007/090614 A1 | 8/2007 |
| WO | WO-2008/087090 A1 | 7/2008 |
| WO | WO-2008/087139 A2 | 7/2008 |
| WO | WO-2008/087140 A2 | 7/2008 |
| WO | WO-2009/027499 A2 | 3/2009 |
| WO | WO-2010/040683 A1 | 4/2010 |
| WO | WO-2010/100226 A1 | 9/2010 |
| WO | WO-2010/100227 A1 | 9/2010 |
| WO | WO-2010/100228 A1 | 9/2010 |
| WO | WO-2010/100229 A1 | 9/2010 |
| WO | WO-2010/100232 A2 | 9/2010 |
| WO | WO-2010/100233 A1 | 9/2010 |
| WO | WO-2010/112406 A1 | 10/2010 |

OTHER PUBLICATIONS

Manz, V.U., "Die anwendung und bedeutung von synthetischen carotinoiden in der lebens- und futtermittel-sowie in der pharmazeutischen industrie," Chimia, 1967, vol. 21, pp. 329-335.
Roy, G.M., Modifying Bitterness: Mechanism, Ingredients, and Applications, Apr. 29, 1997, CRC Press.

\* cited by examiner

PULVERULENT CAROTENOID PREPARATION FOR COLOURING DRINKS

CROSS-REFERENCE TO RELATED APPLICATIONS

This application is a national stage application (under 35 U.S.C. § 371) of PCT/EP2008/065285, filed Nov. 11, 2008, which claims benefit of European application 07121904.2, filed Nov. 29, 2007.

BACKGROUND OF THE INVENTION

The present invention relates to pulverulent compositions of at least one carotenoid selected from the group consisting of β-carotene, astaxanthin, canthaxanthin, citranaxanthin, lycopene and lutein, a process for the production of these pulverulent compositions, and the use of the pulverulent compositions.

The class of substances of carotenoids is classified into two main groups, carotenes and xanthophylls. In contrast to the carotenes, which are pure polyene hydrocarbons, such as, for example, β-carotene or lycopene, in the xanthophylls, oxygen functions such as hydroxyl, epoxy and/or carbonyl groups also occur. Typical representatives of this group are, inter alia, astaxanthin, canthaxanthin, lutein and zeaxanthin.

Lycopene is the dye which gives tomatoes and rosehips their red color. Lutein is an orange-yellow dye which is found, inter alia, in the petals of marigolds (Tagetes), and can be obtained therefrom.

These polyenes which can not only be synthesized but can also be isolated from natural sources are important dyes and active compounds for the food and feed industry and also for the pharmaceutical sector, as in the case of astaxanthin, active compounds having provitamin A activity in salmon.

Not only carotenes but also xanthophylls are insoluble in water, whereas, however, only low solubility is found in fats and oils. This restricted solubility and also the high sensitivity to oxidation stand in the way of direct application of the relatively coarse-grained products obtained by chemical synthesis in coloring foods and feeds, since the substances are not storage stable in coarsely crystalline form and deliver only poor coloring results. These effects which are disadvantageous for practical use of carotenoids are expressed, in particular, in the aqueous medium.

Only by means of specifically produced compositions in which the active compounds are present in finely divided form and, if appropriate, protected against oxidation by protective colloids, may improved color yields be achieved in the direct coloring of foods. In addition, these compositions used in feeds lead to a higher bioavailability of carotenoids, that is to say of carotenes or xanthophylls, and thereby indirectly to better coloring effects, for example in the pigmentation of egg yolks or fish.

To improve the color yields and increase in the resorbability and bioavailability, various processes have been described which all have the purpose of decreasing the crystallite size of the active compounds and bringing it to a particle size range of less than 10 μm.

Numerous methods, described, inter alia, in Chimia 21, 329 (1967), WO 91/06292 and also in WO 94/19411, make use of the grinding of carotenoids by means of a colloid mill and achieve thereby particle sizes of 2 to 10 μm.

WO 2007/003543 describes a grinding process in which β-carotene is comminuted as a suspension to a particle size of about 0.6 μm by grinding in the presence of sucrose or glucose and modified starch, and the carotenoid-comprising suspension is subsequently converted to a dry powder. The resultant powders exhibit, with respect to β-carotene, good storage stability in multivitamin tablets.

In addition to the grinding processes, a number of combined emulsifying/spray-drying processes exist as are described, for example, in DE-A-12 11 911 or in EP-A-0 410 236.

According to the European patent EP-B-0 065 193, finely divided pulverulent carotenoid preparations are produced by a carotenoid being dissolved in a volatile, water-miscible organic solvent at elevated temperatures, if appropriate at elevated pressure, the carotenoid being precipitated out by mixing it with an aqueous solution of a protective colloid and subsequently spray dried.

A similar process for producing finely divided pulverulent carotenoid preparations is described in EP-A-0 937 412, using water-immiscible solvents.

U.S. Pat. No. 6,235,315 describes storage-stable, pulverulent lycopene formulations which, as protective colloid, comprise fish gelatin, and as plasticizer, glucose.

Despite the carotenoid formulations described in the prior art at the outset, on the part of the drinks industry there continues to be a need for improved compositions, in particular pulverulent formulations of lycopene or lutein, which may be dissolved readily in water, in particular cold water, which are also usable in drinks having high water hardness, which exhibit high color intensity or form stable emulsions in the finished drinks, and which, in addition, are free from gelatin.

BRIEF SUMMARY OF THE INVENTION

This object is achieved by a pulverulent composition comprising:

| | |
|---|---|
| 1 to 20% by weight | of at least one carotenoid selected from the group consisting of β-carotene, astaxanthin, canthaxanthin, citranaxanthin, lycopene and lutein, |
| 3 to 60% by weight | of modified starch, |
| 3 to 60% by weight | of glucose, |
| 0.5 to 10% by weight | of at least one antioxidant, and |
| 0.5 to 6.5% by weight | of water-residual moisture, | wherein the percentages by weight relate to the dried powder still comprising residual moisture and where
the weight ratio of the carotenoids to the modified starch is 1:3 to 1:7, preferably 1:3 to 1:5.

DETAILED DESCRIPTION OF THE INVENTION

The pulverulent composition according to the invention comprises 1 to 20% by weight, preferably 5 to 15% by weight, in particular 8 to 13% by weight, of a carotenoid selected from the group consisting of β-carotene, astaxanthin, canthaxanthin, citranaxanthin, lycopene and lutein, preferably selected from the group consisting of lycopene and lutein. In particular, the carotenoid is lycopene.

In addition, the pulverulent composition according to the invention comprises 3 to 60% by weight, preferably 20 to 55% by weight, particularly preferably 30 to 50% by weight, in particular 35 to 45% by weight, of modified starch.

Modified starch is taken to mean chemically or enzymatically produced modification products of starch. These can be starch ethers, starch esters or starch phosphates. Preferred representatives of this group are starch esters, in particular octenyl succinate starch such as, for example, Capsul® (sodium octenyl succinate starch) or Purity® Gum 2000 (sodium octenyl succinate starch) from National Starch, in particular a sodium octenyl succinate starch such as Purity® Gum 2000.

The pulverulent composition according to the invention comprises 3 to 60% by weight, preferably 20 to 55% by weight, particularly preferably 30 to 50% by weight, in particular 35 to 45% by weight, of glucose.

In addition, the pulverulent composition according to the invention comprises 0.5 to 10% by weight, preferably 0.7 to 5% by weight, particularly preferably 0.8 to 2.5% by weight, very particularly preferably 1 to 2% by weight, of at least one antioxidant. Examples of suitable antioxidants are, inter glia, alpha-tocopherol, tertiary butylated hydroxytoluene, tertiary butylated hydroxyanisole, citric acid, sodium citrate, ascorbic acid, sodium ascorbate, ascorbyl palmitate or ethoxyquin or mixtures thereof. Preferred antioxidants are alpha-tocopherol, ascorbic acid, sodium ascorbate, ascorbyl palmitate or mixtures thereof. Very particular preference is given to the antioxidant alpha-tocopherol.

In addition, the pulverulent composition according to the invention comprises 0.5 to 6.5% by weight of water-residual moisture.

For increasing the stability of the pulverulent composition toward microbial breakdown, it can be expedient to add to the composition preservatives such as, for example, methyl 4-hydroxybenzoate, propyl 4-hydroxybenzoate, sorbic acid or benzoic acid, or salts thereof.

The pulverulent composition according to the invention can, if appropriate, also comprise emulsifiers which are used in select cases, preferably in the production of the dispersion. Examples of emulsifiers are ascorbyl palmitate, polyglycerol esters of fatty acids, such as polyglycerol-3 polyricinoleate (PGPR 90), sorbitan esters of fatty acids, such as sorbitan monostearate (span 60), PEG(20) sorbitol monooleate, propylene glycol esters of fatty acids, or phospholipids, such as lecithin.

In addition to the modified starch, the aqueous suspensions according to the invention and the pulverulent compositions produced therefrom can comprise further protective colloids. The following substances, for example, come into consideration therefor:

beef, hog or fish gelatin, in particular gelatin degraded under acid or basic conditions and having Bloom numbers in the range from 0 to 250, very particularly preferably gelatin A 100, A 200, A 240, B 100 and B 200, and also low-molecular-weight, enzymatically degraded gelatin types having the Bloom number 0 and molecular weights of 15 000 to 25 000 D such as, for example, Collagel A and Gelitasol P (from Stoess, Eberbach) and also mixtures of these gelatin varieties.

Starch, dextrin, pectin, gum arabic, ligninsulfonates, chitosan, polystyrenesulfonate, alginates, casein, caseinate, methylcellulose, carboxymethylcellulose, hydroxypropylcellulose, or mixtures of these protective colloids.

Plant proteins such as soy, rice and/or wheat proteins, wherein these plant proteins can be present in partially broken down form, or in non-broken down form.

In the pulverulent composition according to the invention, the weight ratio of modified starch to glucose is preferably 4:1 to 1:3, in particular 1.5:1 to 1:1.5.

Particular preference is given to a pulverulent composition according to the invention as described above, wherein the content of carotenoids in the preparation is 8 to 13% by weight, and the weight ratio of carotenoids to modified starch is 1:3 to 1:5, and the weight ratio of modified starch to glucose is 1.5:1 to 1:1.5.

In the pulverulent composition according to the invention, the carotenoid is preferably present as nanoparticulate particles.

Nanoparticulate particles are taken to mean those particles which have a median particle size D[4,3] determined via Fraunhofer diffraction of 0.02 to 100 μm, preferably 0.05 to 50 μm, very particularly preferably 0.05 to 20 μm, very particularly preferably 0.05 to 5 μm, in particular 0.05 to 1.0 μm. The expression D[4,3] designates the volume-weighted median diameter (see handbook for the Malvern Mastersizer S, Malvern Instruments Ltd., UK).

Preferably, the carotenoid particles in the pulverulent composition according to the invention have a median particle size D[4,3] of 0.07 to 0.7 μm.

The invention further relates to a process for producing the above-described pulverulent composition comprising:

| | |
|---|---|
| 1 to 20% by weight | of at least one carotenoid selected from the group consisting of β-carotene, astaxanthin, canthaxanthin, citranaxanthin, lycopene and lutein, |
| 3 to 60% by weight | of modified starch, |
| 3 to 60% by weight | of glucose, |
| 0.5 to 10% by weight | of at least one antioxidant, and |
| 0.5 to 6.5% by weight | of water-residual moisture, | wherein the percentages by weight relate to the dried powder still comprising residual moisture and where
the weight ratio of the carotenoids to the modified starch is 1:3 to 1:7, comprising the steps
- a₁) dissolving the carotenoids in a water-miscible organic solvent or in a mixture of water and a water-miscible organic solvent at temperatures above 30° C., or
- a₂) dissolving the carotenoids in a water-immiscible organic solvent,
- b) mixing the solution obtained according to a₁) or a₂) with an aqueous molecularly disperse or colloidally disperse solution of a mixture of glucose and the modified starch, wherein the hydrophobic phase of the carotenoids is formed as nanodisperse phase,
- c) converting the dispersion formed into a dry powder by separating off the majority of the water and, if appropriate, solvents additionally used, and subsequent drying.

Preferred embodiments with respect to the components carotenoid, modified starch, glucose and antioxidant and their amounts used may be found in the explanations already made at the outset.

The water-miscible solvents used in stage a₁) of the process according to the invention are, in particular, water-miscible, thermally stable, volatile solvents which only comprise carbon, hydrogen and oxygen, such as alcohols, ethers, esters, ketones or acetals. Expediently, use is made of those solvents which are at least 10% water-miscible, have a boiling point below 200° C. and/or have fewer than 10 carbon atoms. Particularly preferably, use is made of methanol, ethanol, n-propanol, isopropanol, 1,2-butanediol 1-methyl ether (1-methoxybutan-2-ol), 1,2-propanediol 1-n-propyl ether (1-propoxy-propan-2-ol), tetrahydrofuran or acetone.

The expression "water-immiscible organic solvent", for the purposes of the present invention, is an organic solvent having a water solubility at atmospheric pressure of less than 10%. Possible solvents which come into consideration are, inter alia, halogenated aliphatic hydrocarbons, such as, for example, methylene chloride, chloroform and carbon tetrachloride, esters of carboxylic acids such as dimethyl carbonate, diethyl carbonate, propylene carbonate, ethyl formate, methyl, ethyl or isopropyl acetate, and also ethers such as methyl tert-butyl ether. Preferred water-immiscible organic solvents are the following compounds from the group consisting of dimethyl carbonate, propylene carbonate, ethyl formate, ethyl acetate, isopropyl acetate and methyl tert-butyl ether.

In the process according to the invention, preferably process step $a_1$) is carried out wherein the carotenoid is dissolved in a water-miscible organic solvent, or in a mixture of water and a water-miscible organic solvent, at temperatures above 30° C., preferably between 50° C. and 240° C., in particular 100° C. to 200° C., particularly preferably 140° C. to 180° C., if appropriate under pressure.

Since the action of high temperatures, under some circumstances can lower the desired high all-trans isomer fraction of the carotenoid, in particular lycopene or lutein, the carotenoid(s) is/are dissolved as rapidly as possible, for example in the range of seconds, e.g. in 0.1 to 10 seconds, particularly preferably in less than 1 second. For rapid production of the molecularly disperse solution, the use of elevated pressure, e.g. in the range from 20 bar to 80 bar, preferably 30 to 60 bar, can be advantageous.

The resultant molecularly disperse solution is admixed subsequently in process step b) directly with the, if appropriate cooled, aqueous molecularly disperse or colloidally disperse solution of the mixture of glucose and modified starch, wherein the hydrophobic phase of the carotenoids is formed as a nanodisperse phase. Preferably, in process step b) a mixture temperature of about 35° C. to 80° C. is established.

The solvent component from process step $a_1$) is transferred into the aqueous phase in this case and the hydrophobic phase of the carotenoid(s) is/are formed as nanodisperse phase.

With respect to a more detailed process and apparatus description with reference to the abovementioned dispersion, reference is made at this point to EP-B-0 065 193.

In the process according to the invention, in process step c), the dispersion formed is converted into a dry powder by separating off the majority of the water and if appropriate solvents additionally used and subsequent drying.

The conversion into a dry powder can proceed, inter alia, via spray drying, spray cooling, modified spray drying, freeze drying or drying in a fluidized bed, if appropriate also in the presence of a coating material. Suitable coating materials are, inter alia, cornstarch, silica or else tricalcium phosphate.

Preferably, in process step c), the dispersion formed is concentrated to a solids concentration of about 20 to 35% by weight by separating off the majority of the water and any solvents additionally present by distillation and subsequently converting this concentrated dispersion into a dry powder in a spray drier.

Particularly preferably, in process step c) of the process according to the invention, the drying is carried out in a spray drier having an integrated and/or downstream external fluidized bed. Preferably, in this case, a pulverulent composition having agglomerated particles is formed. The resultant agglomerated particles preferably have, depending on the apparatus used, the structure of an onion, a raspberry, a compact cluster or a loose cluster. These agglomerate structure types, the resultant powder properties and also agglomeration behavior are described, for example, by Ejnar Refstrup, "Recent Advances in Agglomeration during Spray Drying", in "Zeitschrift für Lebensmitteltechnologie", ZFL 43 (1992), 10, pages 576 to 582. The agglomerated particles of the pulverulent composition according to the invention have, particularly preferably, the structure of a raspberry or a compact or loose cluster, in particular a compact or loose cluster.

The dry powders according to the invention may be redispersed again in a problem-free manner in aqueous systems, achieving a uniform fine distribution of the active compound in the particle size range smaller than 1 μm. It may be noted in this case that the dry powders according to the invention may be redispersed very rapidly in cold water and form dispersions which are stable over a long time and have high color strength.

The pulverulent composition according to the invention is suitable, inter alia, as additive to food compositions, for example for coloring foods such as drinks, as means for producing pharmaceutical and cosmetic compositions, and also for the production of food supplement preparations, for example multivitamin preparations in the human and animal sectors. Preferably, the pulverulent composition is suitable as additive to drinks.

The present invention therefore further relates also to the use of the above-described pulverulent composition according to the invention as additive to animal feeds, foods, food supplements or pharmaceutical compositions, in particular as additive to drinks.

The present invention likewise relates to animal feeds, foods, food supplements or pharmaceutical compositions, in particular a drink, which comprises the pulverulent composition according to the invention.

The invention will be explained by the following examples which are, however, not restrictive:

EXAMPLES

Example 1

10 g of crystalline lycopene were suspended in a solution of 1.7 g of α-tocopherol and 130 g of isopropanol. This suspension was mixed at a transport rate of 1.5 kg/h and 50 bar system pressure with 460 g of hot isopropanol (transport rate 2.6 kg/h) to give a solution temperature of 170° C. This solution was mixed turbulently in a mixing chamber with a solution of 70.4 g of Purity Gum 2000 (National Starch) and 80.4 g of glucose in 6450 g of water. The isopropanol was subsequently removed from this lycopene dispersion by means of a vacuum evaporator, and the dispersion converted into a powder by spray drying. The lycopene content in the powder was 10.9% and the median particle size of the lycopene particles was 307 nm.

The invention claimed is:
1. A pulverulent composition comprising:

| | |
|---|---|
| 1 to 20% by weight | of at least one carotenoid selected from the group consisting of β-carotene, astaxanthin, canthaxanthin, citranaxanthin, lycopene and lutein, |
| 3 to 60% by weight | of modified starch, |
| 3 to 60% by weight | of glucose, |
| 0.5 to 10% by weight | of at least one antioxidant, and |
| 0.5 to 6.5% by weight | of water-residual moisture, | wherein the percentages by weight relate to the dried powder still comprising residual moisture and wherein the weight ratio of the carotenoids to the modified starch is 1:3 to 1:7.

2. The pulverulent composition according to claim 1, wherein the carotenoid is lycopene.

3. The pulverulent composition according to claim 1, wherein the modified starch is an octenyl succinate starch.

4. The pulverulent composition according to claim 1, wherein the antioxidant is alpha-Tocopherol.

5. The pulverulent composition according to claim 2, wherein the modified starch is an octenyl succinate starch and the antioxidant is alpha-Tocopherol.

6. The pulverulent composition according to claim 1, wherein the weight ratio of modified starch to glucose is 4:1 to 1:3.

7. The pulverulent composition according to claim 1, wherein the content of carotenoids in the composition is 8 to 13% by weight, and the weight ratio of the carotenoids to modified starch is 1:3 to 1:5 and the weight ratio of modified starch to glucose is 1.5:1 to 1:1.5.

8. The pulverulent composition according to claim 5, wherein the content of carotenoids in the composition is 8 to 13% by weight, and the weight ratio of the carotenoids to modified starch is 1:3 to 1:5 and the weight ratio of modified starch to glucose is 1.5:1 to 1:1.5.

9. An animal feed, food, food supplement or pharmaceutical composition comprising the pulverulent composition defined according to claim 1.

10. A drink comprising the pulverulent composition defined according to claim 1.

11. The pulverulent composition according to claim 1, wherein the carotenoid is present as nanoparticulate particles with a median particle size of 0.07 to 0.7 µm.

12. The pulverulent composition according to claim 1, wherein glucose is present in an amount from 30 to 60% by weight.

13. The pulverulent composition according to claim 1, wherein glucose is present in an amount from 30 to 50% by weight.

14. The pulverulent composition according to claim 1, wherein glucose is present in an amount from 35 to 60% by weight.

15. The pulverulent composition according to claim 1, wherein glucose is present in an amount from 35 to 45% by weight.

16. The pulverulent composition according to claim 1, wherein the composition is produced by a process comprising the steps
 $a_1$) dissolving the carotenoids in a water-miscible organic solvent or in a mixture of water and a water-miscible organic solvent at temperatures above 30° C. or
 $a_2$) dissolving the carotenoids in a water-immiscible organic solvent selected from the group consisting of dimethyl carbonate, propylene carbonate, ethyl formate, ethyl acetate, isopropyl acetate and methyl tert-butyl ether,
 b) mixing the solution obtained according to $a_1$) and $a_2$) with an aqueous molecularly disperse or colloidally disperse solution of a mixture of glucose and the modified starch, wherein the hydrophobic phase of the carotenoids is formed as nanodisperse phase,
 c) converting the dispersion formed into a dry powder by separating off the majority of the water and, optionally, solvents additionally used, and subsequent drying.

17. The pulverulent composition according to claim 16, wherein composition is produced by steps a1), b) and c).

18. A pulverulent composition comprising:

| | |
|---|---|
| 1 to 20% by weight | of at least one carotenoid selected from the group consisting of β-carotene, astaxanthin, canthaxanthin, citranaxanthin, lycopene and lutein, |
| 3 to 60% by weight | of modified starch, |
| 20 to 55% by weight | of glucose, |
| 0.5 to 10% by weight | of at least one antioxidant, and |
| 0.5 to 6.5% by weight | of water-residual moisture, | wherein the percentages by weight relate to the dried powder still comprising residual moisture and wherein the weight ratio of the carotenoids to the modified starch is 1:3 to 1:7 produced by a process comprising the steps
 a) dissolving the carotenoids in a water-miscible organic solvent or in a mixture of water and a water-miscible organic solvent at temperatures above 30° C.,
 b) mixing the solution obtained according to a) with an aqueous molecularly disperse or colloidally disperse solution of a mixture of glucose and the modified starch, wherein the hydrophobic phase of the carotenoids is formed as nanodisperse phase, and
 c) converting the dispersion formed into a dry powder by separating off the majority of the water and, optionally, solvents additionally used, and subsequent drying.

19. The pulverulent composition according to claim 17, wherein in step c), the dispersion formed is concentrated to a solids concentration of about 20 to 35% by weight by separating off the majority of the water and any solvents additionally present by distillation and subsequently converting this concentrated dispersion into a dry powder in a spray drier.

20. A pulverulent composition consisting essentially of:

| | |
|---|---|
| 8 to 12% by weight | of lycopene, |
| 35 to 45% by weight | of octenyl succinate starch and |
| 35 to 45% by weight | of glucose, |
| 1 to 2% by weight | of at alpha-Tocopherol, and |
| 0.5 to 6.5% by weight | of water-residual moisture, | wherein the percentages by weight relate to the dried powder still comprising residual moisture and wherein the weight ratio of the lycopene to the octenyl succinate starch is 1:3 to 1:5 and wherein the lycopene is present as nanoparticulate particles with a median particle size of 0.07 to 0.7 µm.

* * * * *